United States Patent [19]
Shaw et al.

[11] Patent Number: 5,611,996
[45] Date of Patent: Mar. 18, 1997

[54] SLIDE TEST ELEMENT HOLDER WITH MINIMIZED Z-AXIS VARIABILITY

[75] Inventors: James D. Shaw; Merrit N. Jacobs, both of Rochester, N.Y.

[73] Assignee: Johnson & Johnson Clinical Diagnostics, Inc., Rochester, N.Y.

[21] Appl. No.: 471,073

[22] Filed: Jun. 6, 1995

[51] Int. Cl.⁶ .................................................... G01N 1/28
[52] U.S. Cl. ............................ 422/63; 422/64; 422/104; 436/46; 436/48
[58] Field of Search ............................ 422/62–65, 68.1, 422/82.02, 82.05, 104; 436/46, 48

[56] References Cited

U.S. PATENT DOCUMENTS

| | | | |
|---|---|---|---|
| 4,296,070 | 10/1981 | Montalto et al. | 422/65 |
| 4,302,420 | 11/1981 | Jakubowicz et al. | 422/63 |
| 4,753,531 | 6/1988 | Hiratsuka et al. | 356/246 |
| 5,030,418 | 7/1991 | Miyata | 422/63 |
| 5,034,191 | 7/1991 | Porte | 422/64 |
| 5,053,198 | 10/1991 | Quenin | 422/64 |
| 5,059,393 | 10/1991 | Quenin et al. | 422/64 |
| 5,081,038 | 1/1992 | Sugaya et al. | 436/46 |
| 5,174,960 | 12/1992 | Shaw et al. | 422/63 |
| 5,244,632 | 9/1993 | Shaw et al. | 422/63 |
| 5,283,195 | 2/1994 | Muszak et al. | 436/48 |

FOREIGN PATENT DOCUMENTS

| | | |
|---|---|---|
| 3717914A1 | 12/1987 | Germany . |
| 61/209341 | 9/1986 | Japan . |

*Primary Examiner*—Harold Pyon
*Attorney, Agent, or Firm*—Dana M. Schmidt

[57] ABSTRACT

A holder of slide test elements for use in an analyzer at a sample-dispensing station, the holder comprising two opposing holding surfaces for holding generally horizontally a slide test element at opposite side edges of the test element, and a tower extending above the holding surfaces for generally centering a dispensing tip above a held slide test element. The holder is improved in that one of the holding surfaces of the holder extends at least sufficiently for underneath a slide test element held by the holding surfaces to be disposed under an approximate center of the held test element, and includes a raised reference surface located under, and disposed for abutting against, an under-surface of the held slide test element, so that a held slide test element is prevented by the raised reference surface from warping downwardly away from a dispensing tip in the tower.

3 Claims, 3 Drawing Sheets

SLIDE TEST ELEMENT HOLDER WITH MINIMIZED Z-AXIS VARIABILITY

FIELD OF THE INVENTION

This invention relates to apparatus for correctly positioning a slide test element at a station for dispensing liquid onto the test element, even if the test element tends to have a bowed shape.

BACKGROUND OF THE INVENTION

It is known, in the field of clinical analyzers, to dispense patient sample onto a dried slide test element using a slide holder that has a metering shoulder that positions a dispensing probe above the slide test element. Such is shown, for example, in U.S. Pat. No. 4,296,070, especially FIGS. 4–6. In such a holder, a slide is fed into the holder only along its two opposite edges, and if the slide is perfectly dimensioned and perfectly flat when inserted, the holder will hold that slide test element at exactly the right vertical distance from the tip of the dispensing probe, during dispensing.

Although such a construction has worked well in the past, it has not accounted for the fact that in a few cases, the dimensional tolerances of the width, or flatness, of the slide test element are such that the slide element ends up being bowed up or down when it is within the holder, ready to receive dispensed liquid. This in turn creates a variable vertical distance between test element and dispensing probe, hereinafter "Z-axis variability". We have discovered that this can be a problem in a) some colorimetric end-point assays, and rate assays, and in b) most immunoassays requiring a wash liquid to be so dispensed. That is, in case a), namely, said some end-point assays, a ring of color will form that has a different density than the rest of the test area. The ring is located at the circumference of the lens formed by the sample contacting the slide test element. Ideally, the ring forms outside the portion of the test area used for reading. However, Z-axis variability can lead, in some cases, to the ring's location falling within, not without, the read area. This, of course, interferes with the precision of the determination of assay concentration.

In case b) regarding washed immunoassays, it is the delivery of the wash liquid by a dispensing probe in the slide holder that is affected by Z-axis variability as described in commonly-owned companion application U.S. Ser. No. 08/393,632, filed on Feb. 24, 1995, entitled, A Method For Washing Immunoassay Elements, by Merrit N. Jacobs et al. It is important, for thorough washing of the center of the wash application, wherever that might be, that the drops of wash be small when contacting the slide test element. However, with many dispensing probes, the size of the drop is controlled by the Z-axis distance as well as the size of the dispensing platform of the tip of the dispenser. If there is Z-axis variability, the initial drop size can easily exceed the nominal small size that is desired, if the Z-axis distance has increased beyond optimum.

For all of the above reasons, it has been a problem prior to this invention that Z-axis variability has not been adequately controlled.

SUMMARY OF THE INVENTION

We have designed a slide holder that overcomes the afore-noted problems.

More specifically, there is provide, in accordance with one aspect of the invention, a holder of slide test elements for use in an analyzer at a sample-dispensing station, the holder comprising two opposing holding surfaces for holding generally horizontally a slide test element at opposite side edges of the test element, and a tower extending above the holding surfaces for generally centering a dispensing tip above a held slide test element. The holder is improved in in that one of the holding surfaces of the holder extends at least sufficiently far horizontally underneath a slide test element held by the holding surfaces to be disposed under an approximate center of the held test element, and includes a raised reference surface located under, and disposed for abutting against, an approximate center of an under-surface of the held slide test element, so that a held slide test element is prevented by the raised reference surface from a dispensing tip in the tower.

Accordingly, it is an advantageous feature of the invention that a slide test element is held at a dispensing station, either for sample dispensing or washing, or both, with a minimum of Z-axis variability.

It is a related advantageous feature that such a slide test element is held, via the invention, so as to reduce variation in ring formation due to sample spreading.

It is another related advantageous feature that such a slide test element is held, via the invention, at a wash station in a manner that prevents initial wash droplets from exceeding their nominal size.

Other advantageous features will become apparent upon reference to the following Description of the Preferred Embodiments, when read in light of the attached drawings.

DESCRIPTION OF THE PREFERRED EMBODIMENTS

The following description is presented of the preferred embodiments, in which the slide test elements are of a preferred type, and in which sample or wash liquid is dispensed from pipette tips of a certain design in a test element holder having a tower for holding the pipette tip. In addition, the invention is applicable regardless of a) the kind of dried slide test element (and the frame therefor) that is used, b) the kind of liquid that is dispensed, c) the kind or even the existence of the pipette tip from which the liquid is dispensed, and d) whether the test element holder is provided or not with a tip-holding tower.

As used herein, "slide test element" means, a flat, relatively thin and flexible, slide-like construct containing dried reagents for producing a change, preferably a colorimetric change in response to an analyte present, if any, in a liquid sample added to the construct, the construct being the entirety of that which is moved into and out of position at a liquid-dispensing station. Because such constructs are thin and flexible, they have the bowing or Z-axis variability problem which this invention solves.

Thus, the preferred slide test elements are the dried colorimetric slide test elements available under the trademark "Ektachem" from Clinical Diagnostic Systems Inc., formerly of Eastman Kodak Co., now a company of Johnson & Johnson. Additionally, those supplied by, for example, Fuji Photo can be used in the invention, with a suitable adjustment in spacing to accommodate the difference in slide thickness. What is not included in this invention is apparatus that processes liquid by depositing it into relatively rigid containers, rather than slides, as shown for example in U.S. Pat. No. 4,753,531 as containers 11, since such containers, due to their rigidity, have no bowing problem and hence no need for the invention. Indeed, due to their thickness they are not dimensioned to work in the invention.

Figure 1:
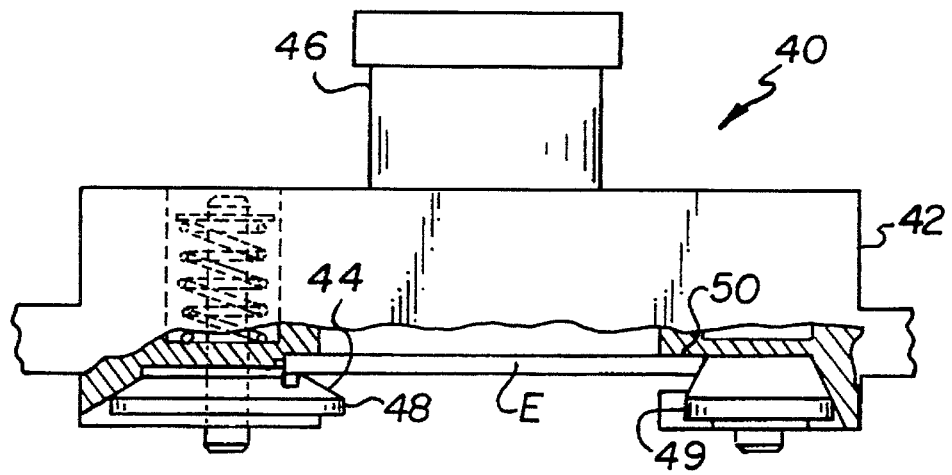
FIG. 1 is a fragmentary elevational view, partially in section, of a slide holder constructed in accordance with the prior art.
Figure 2:
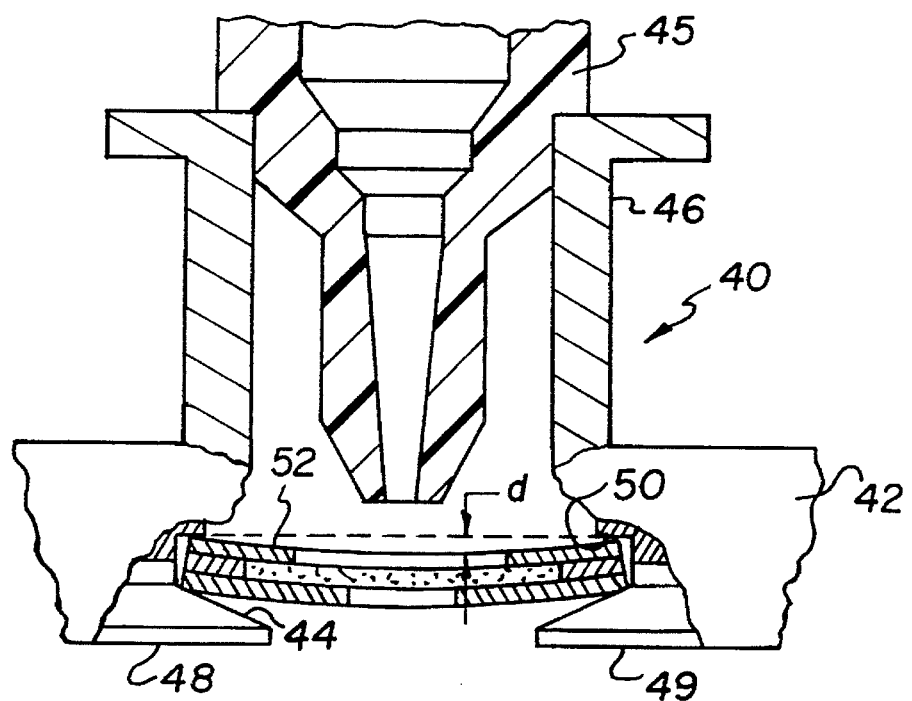
FIG. 2 is a fragmentary elevational view similar to that of FIG. 1, except it is enlarged to show greater detail.
Figure 3:
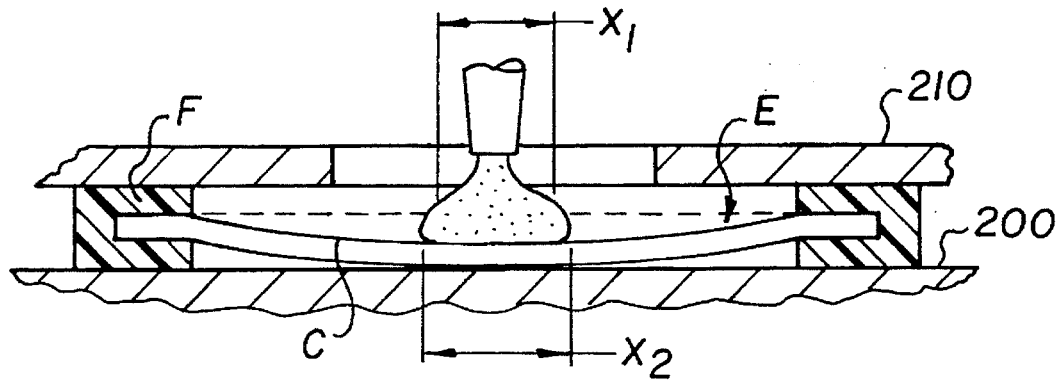
FIG. 3 is a schematic illustration of the test element and dispensing tip of FIG. 2, in the same prior art holder, showing one aspect of drawbacks of said holder.

FIGS. 1–3 illustrate the prior art. As shown in e.g., the aforesaid '070 patent, a conventional test element holder 40 comprises a housing 42, a tower 46 extending upwardly therefrom to hold a pipette tip 45 in proper vertical position for dispensing, FIG. 2, and opposing surfaces 44 and 50 of housing 42 that holds a test element E in place the proper vertical distance away from and under tip 45. Surface 50 can be any flat, horizontal undersurface of housing 42, as shown in FIG. 2. Surface 44 is preferably a camming surface angled with respect to the plane of surface 50, and mounted on a pair of rollers 48,49. Such rollers and camming surfaces force a test element E as it enters holder 40, to move up into contact with surface 50, FIG. 1.

However, problems, though not common, can occur in such a construction. Occasionally a test element E', FIG. 2, is warped or otherwise bowed, either as manufactured or as positioned in holder 40. As a result, element E' has a top surface 52 that can be bowed down away from its optimal location, shown in phantom, to its position shown in solid lines, spaced a distance "d" away from the optimal position. "d" is the amount of Z-axis variability in this example. This in turn can lead to an undesirable alteration in the interface between a dispensed drop of liquid, FIG. 3, and the held test element. Specifically, when a test element is bowed downward, the drop contacts the test element with a larger diameter $X_2$, instead of the expected, optimum diameter $X_1$. This can be particularly serious when the liquid is a wash liquid, since as is explained in the aforesaid companion application, wash droplets perform better if they are small, rather than large.

Alternatively, the bowing can be upward (not shown). As will be readily apparent, such a version of the Z-axis variability reduces the diameter of the contacting liquid drop to some value less than x. This is undesirable particularly in dispensing sample, because the resulting reduction in diameter causes the ring formation in color development (if any) to occur at reduced distances from center, such that the ring can end up being at variable locations within the area of detection by the reflectometer, decreasing precision.

The Invention

Figure 4:
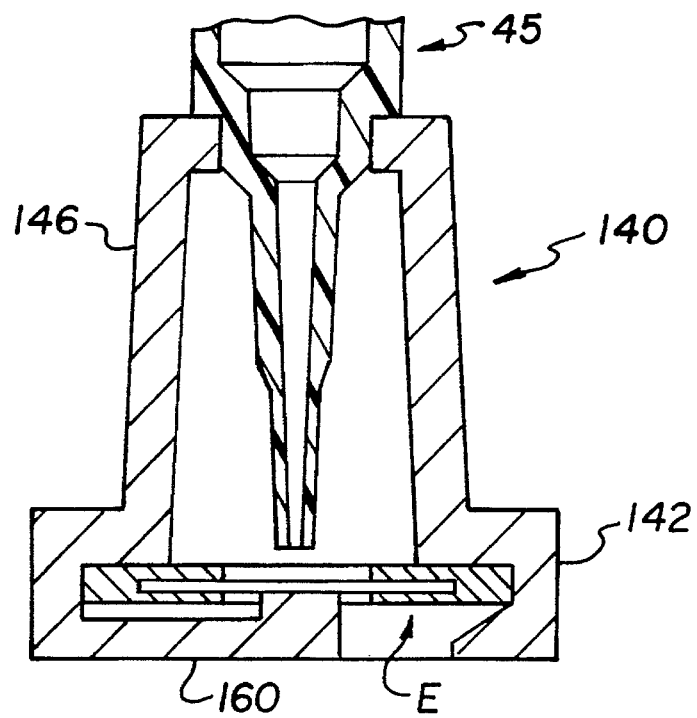
FIG. 4 is a fragmentary elevational view similar to that of FIG. 1, illustrating however one embodiment of the slide holder of the invention.
Figure 5:
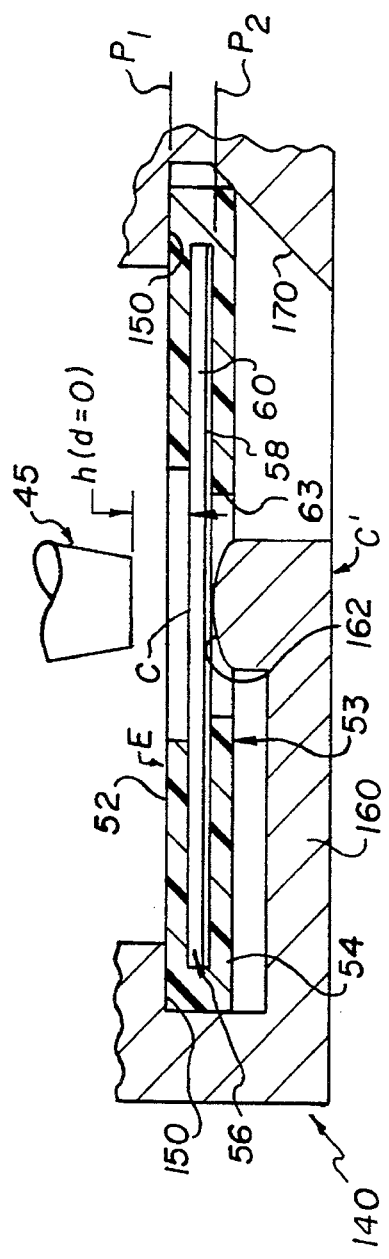
FIG. 5 is an enlarged fragmentary elevational view of the view of FIG. 4.

In accordance with one aspect of the invention, the test element holder is modified, FIGS. 4 and 5, to provide for a supporting surface that corrects for the bowing. In this particular embodiment, holder 140 has a housing 142 and tower 146 constructed similarly to holder 40 of FIG. 1 to vertically position a (the same) pipette tip 45 from a (the same) slide test element E. Thus, two top surfaces 150 are provided by two shoulders located in a generally horizontal plane against which the upper surface 52 of held element E is to abut, FIG. 5. (Surfaces 150 can also be curved, not shown.)

However, the underneath surface provided by housing 142 is altered. It includes a rigid, inflexible ledge 160 that projects at least out to a position C' disposed under the approximate center "C" of element E. A raised, biasing or reference surface 62 is provided at position C', for contacting the under-surface 53 of element E. Those knowledgeable in the art will recognize that such elements E comprise a plastic frame 54 with a lower viewing aperture 63, and a chemistry chip 56 captured inside of the frame, the chip in turn comprising a plastic support layer 58, usually "Estar" polyethylene terephthalate, on which is coated one or more porous layers 60. It is plastic layer 58 that raised surface 62 presses against to keep element E from bowing downward. Preferably, surface 162 is curved rather than formed with right-angle corners, to allow smooth movement of aperture 63 onto and off of surface 162 as element E moves into and out of, respectively, holder 140.

Still further, the lower support of housing 140 optionally includes a fixed camming surface 170 that acts to cam a held test element E up against lower surface 150. Alternatively (not shown), surface 170 can be part of a roller as shown in FIG. 1 (the prior art).

Together surfaces 150 and 162 ensure that surface 53 of element E is always in contact in plane P2 with surface 162 of the raised portion of ledge 160. To this end, the spacing between surface 150 and surface 162 is preferably less than the minimum distance surface 150 can be from surface 52, even if element E is bowed upward. As a result, the spacing "h", FIG. 5, between the end of tip 45 and the top surface of layer 60, is properly and predictably maintained—that is, Z-axis variability "d" is kept at or near zero in value.

Figure 6:
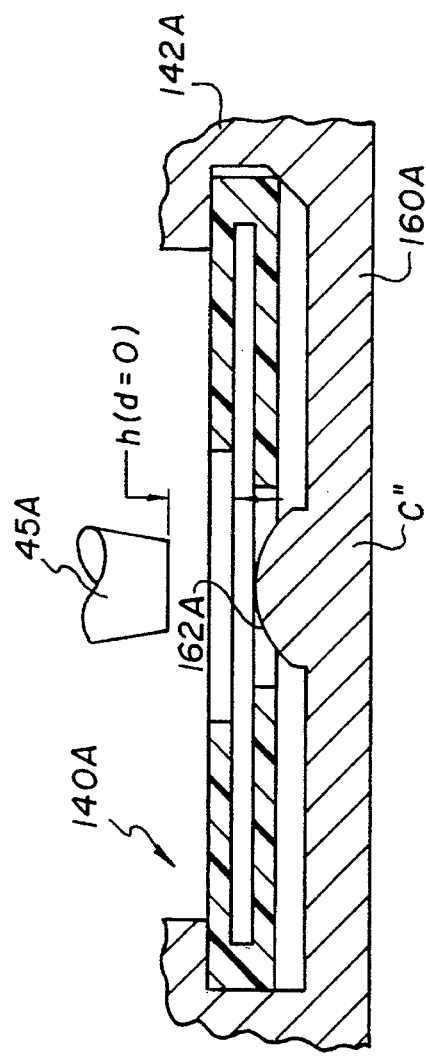
FIG. 6 is a fragmentary elevational view similar to that of FIG. 4, but illustrating another embodiment of the invention.

The ledge 160 need not be only a partial ledge, but can extend completely across under element E, as shown in FIG. 6. Parts similar to those previously described bear the same reference numerals, to which the distinguishing suffix "A" is appended.

Thus, holder 140A and housing 142A are constructed as in FIG. 5, except that ledge 160A extends completely across underneath a held element E, and raised surface 162A is disposed approximately in the center "C" of surface 160A. As in the embodiment of FIG. 5, Z-axis variability "d" is substantially zero. With this embodiment, it is possible to make ledge 160A transparent to allow a scan of the test element through ledge 160A, while the test element is still at holder 140A.

FIG. 3 illustrates a comparative example, as well as the prior art. That is, in FIG. 3, a supporting surface 200 is disposed underneath, and in contact with, frame F of test element E. Additionally, a blade 210 is disposed above and in contact with the top surface of frame f, so as to hold and keep frame F from bowing, presumably. But, no attempt is made to have a support at the CENTER of the test element, that is, in contact with the "Estar" film support layer that is the bottom of the chemistry chip of element E. The result is, that chip C of element E can and often is bowed out of the center plane, i.e., downwardly as shown, producing the unfortunate results described above in the "Background".

Such bowing of only the chip C is caused by the firm attachment of the frame F to chip C, in a manner that gives no degree of freedom for any horizontal stress in chip C, thus forcing it out of plane.

Yet another alternative, not shown, is to replace the shoulders providing the fixed surfaces 150, with a pair of springs delivering a light spring force downward against the edges of a slide test element inserted between the springs and raised surfaces 162.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. In a holder of slide test elements for use in an analyzer at a sample-dispensing station, said holder comprising two opposing holding surfaces for holding generally horizontally a slide test element at opposite side edges of the test element, and a tower extending above said holding surfaces for generally centering a dispensing tip above a held slide test element, the improvement wherein one of said holding surfaces of said holder extends at least sufficiently far horizontally underneath a slide test element held by said holding surfaces to be disposed under an approximate center of said held test element, said one holding surface including a raised reference surface located under, and disposed for abutting against, an approximate center of an under-surface of said held slide test element, said raised reference surface being spaced away from the other of said holding surfaces a distance which ensures that said raised reference surface always contacts the under surface of a held test element so that a held slide test element is prevented by said raised reference surface from warping downwardly away at said approximate center, from a dispensing tip in said tower.

2. A slide holder as defined in claim 1, wherein said slide test element includes a plastic support layer and said raised surface contacts said plastic support layer.

3. A slide holder as defined in claim 1, wherein said one holding surface extends completely underneath all of said held test element.

\* \* \* \* \*